(12) United States Patent
Gelles

(10) Patent No.: US 7,348,376 B2
(45) Date of Patent: Mar. 25, 2008

(54) ADHESIVE COMPOSITION

(75) Inventor: Richard Gelles, Houston, TX (US)

(73) Assignee: Kraton Polymers U.S. LLC, Houston, TX (US)

( * ) Notice: Subject to any disclaimer, the term of this patent is extended or adjusted under 35 U.S.C. 154(b) by 451 days.

(21) Appl. No.: 10/823,146

(22) Filed: Apr. 13, 2004

(65) Prior Publication Data

US 2005/0228114 A1  Oct. 13, 2005

(51) Int. Cl.
*C08L 9/00* (2006.01)

(52) U.S. Cl. ......................................... 524/505; 525/98

(58) Field of Classification Search ................ 524/505; 525/98
See application file for complete search history.

(56) References Cited

U.S. PATENT DOCUMENTS

| | | | |
|---|---|---|---|
| 3,149,182 A | 9/1964 | Porter | 260/879 |
| 4,188,432 A | 2/1980 | Holden et al. | 428/35 |
| 4,857,594 A | 8/1989 | Lakshmanan et al. | 525/98 |
| 6,329,468 B1 | 12/2001 | Wang | |
| 6,455,627 B1 | 9/2002 | De Keyzer et al. | 524/505 |
| 6,465,557 B1 | 10/2002 | De Keyzer et al. | |
| 6,582,829 B1 | 6/2003 | Quinn et al. | 428/513 |
| 6,653,385 B2 | 11/2003 | Wang et al. | |
| 6,657,000 B1 | 12/2003 | De Keyzer et al. | 524/505 |

FOREIGN PATENT DOCUMENTS

| | | |
|---|---|---|
| EP | 1331258 | 7/2003 |
| WO | WO01/00257 | 1/2001 |

*Primary Examiner*—Peter D. Mulcahy
(74) *Attorney, Agent, or Firm*—Donna Blalock Holguin; Michael A. Masse

(57) ABSTRACT

Disclosed is an adhesive comprising an admixture of a high vinyl selectively hydrogenated block copolymer and an amorphous polyolefin. The high vinyl content of the block copolymer results in a more compatible admixture which in turn results in an adhesive that can be more easily processed than those prepared using conventional lower vinyl content block copolymers. The adhesives of the present invention can be prepared using less or even no compatibilizing additives which allows the adhesives to be used in end uses where such additives are undesirable.

30 Claims, No Drawings

ADHESIVE COMPOSITION

BACKGROUND OF THE INVENTION

1. Field of the Invention

This invention relates to adhesive compositions. This invention particularly relates to adhesive compositions including block copolymers.

2. Background of the Art

The preparation of block copolymers of mono alkenyl arenes and conjugated dienes is well known. One of the first patents on linear ABA block copolymers made with styrene and butadiene is U.S. Pat. No. 3,149,182. Uses for the block copolymers include injection molding, extrusion, blow molding, adhesives, and the like. These polymers have also been used in applications such as the modification of bitumen for the production of roofs and roads. Other uses of block copolymers include the production of films, fibers, non-woven fabrics.

One early example of such a block copolymer is in U. S. Pat. No. 4,188,432 to Holden, et al. Disclosed therein are shaped articles which are resistant to attack by fatty substances consisting essentially of high impact styrene-butadiene graft copolymer or a mixture thereof with no more than about 55% styrene homopolymer. The shaped articles also include small proportions of polyethylene or polypropylene and of a block copolymer X-Y-X in which each X is a polystyrene block of about 5,000 to 10,000 molecular weight and Y is a hydrogenated polybutadiene block of 25,000 to 50,000 molecular weight.

Adhesive compositions based on styrenic block copolymers as thermoplastic elastomer components are well known in the art. These compositions are disclosed to be useful for preparing pressure sensitive adhesives for industrial tapes, packaging tapes and labels, and in multipurpose hot-melt adhesive compositions which may be used to bond or construct articles in the manufacture of disposable soft goods, such as diapers, feminine care articles, surgical drapes and the like. Styrene-isoprene-styrene block copolymers and styrene-butadiene-styrene block copolymers are widely used in these adhesive compositions.

EP-1331000258 to Muyldermans, et al., discloses a pressure sensitive adhesive composition comprising, calculated on 100% of all the components, 30 to 45% of one or more block copolymers of structure ABA or (AB) (n)-X or ABABA or BABAB or ABAB were each A independently is a polymer block of a monoalkenyl arene; each B independently is a polymer block of a conjugated diene, or a mixture of conjugated dienes, hydrogenated in such a manner to leave a residual unsaturation content below 20%. It is also disclosed therein that the adhesive can include an optional and additional component such as a polyolefin.

U.S. Pat. No. 6,657,000 to De Keyzer, et al., also discloses an adhesive including a block copolymer. This reference discloses a hot melt pressure sensitive positioning adhesive for use with an absorbent article. The adhesive comprises: (a) from 5 to less than 15 percent by weight of a blend of (i) a hydrogenated styrene-(butadiene or isoprene)-styrene block copolymer having a polystyrene block number average molecular weight of 20,000 or less, and (ii) a homogeneous linear or substantially linear interpolymer of ethylene and at least one $C_3$-$C_{20}$ alpha olefin having a density from 0.85 to 0.91 grams per cubic centimeter; and (b) from 50 to 80 percent by weight of a tackifying resin and (c) from 5 to 35 percent by weight of a plasticizing oil. The block copolymer of (i) may also be one in which the polystyrene block molecular weight is greater than 20,000.

U. S. Patent No. 6,582,829 to Quinn, et al., discloses a hot melt adhesive composition comprising homogeneous ethylene interpolymer and a block copolymer. The hot melt adhesive composition is one comprising a) from about 5 wt-% to about 50 wt-% of at least one homogeneous linear or substantially linear ethylene/alpha-olefin interpolymer characterized as having a density from 0.850 to 0.965 g/cm³; b) from about 1 wt-% to about 40 wt-% of at least one block copolymer; and c) from about 10 wt-% to about 75 wt-% of at least one tackifying resin. The adhesive is further characterized in that it does not fail cohesively.

SUMMARY OF THE INVENTION

In one aspect, the present invention is an adhesive comprising an amorphous polyolefin and a selectively hydrogenated block copolymer having an S block and an E or $E_1$ block and having the general formula:

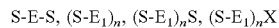

S-E-S, (S-$E_1$)$_n$, (S-$E_1$)$_n$S, (S-$E_1$)$_n$X or mixtures thereof, wherein: (a) prior to hydrogenation the S block is a polystyrene block; (b) prior to hydrogenation the E block is a polydiene block, selected from the group consisting of polybutadiene, polyisoprene and mixtures thereof, having a molecular weight of from 40,000 to 120,000 daltons;(c) prior to hydrogenation the $E_1$ block is a polydiene block, selected from the group consisting of polybutadiene, polyisoprene and mixtures thereof, having a molecular weight of from 20,000 to 60,000 daltons; (d) n is an integer having a value of 2 to 6 and X is a coupling agent residue; (e) the styrene content of the block copolymer is from 10 percent to 40 weight percent; (f) the vinyl content of the polydiene block prior to hydrogenation is from 72 to 90 mole percent; (g) the block copolymer includes less than 25 weight percent lower molecular weight units having the general formula:

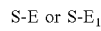

S-E or S-$E_1$ wherein S, E and $E_1$ are as already defined; (h) subsequent to hydrogenation about 0-10% of the styrene double bonds have been hydrogenated and at least 80% of the conjugated diene double bonds have been hydrogenated; and (i) the molecular weight of each of the S blocks is from 4,000 to 12,000 daltons.

In another aspect, the present invention is an article of manufacture comprising a substrate and adherent thereto an adhesive comprising an amorphous polyolefin and a selectively hydrogenated block copolymer having an S block and an E or $E_1$ block and having the general formula:

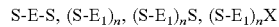

S-E-S, (S-$E_1$)$_n$, (S-$E_1$)$_n$S, (S-$E_1$)$_n$X or mixtures thereof, wherein: (a) prior to hydrogenation the S block is a polystyrene block; (b) prior to hydrogenation the E block is a polydiene block, selected from the group consisting of polybutadiene, polyisoprene and mixtures thereof, having a molecular weight of from 40,000 to 120,000 daltons;(c) prior to hydrogenation the $E_1$ block is a polydiene block, selected from the group consisting of polybutadiene, polyisoprene and mixtures thereof, having a molecular weight of from 20,000 to 60,000 daltons; (d) n is an integer having a value of 2 to 6 and X is a coupling agent residue; (e) the styrene content of the block copolymer is from 10 percent to 40 weight percent; (f) the vinyl content of the polydiene block prior to hydrogenation is from 72 to 90 mole percent; (g) the block copolymer includes less than 25 weight percent lower molecular weight units having the general formula:

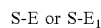

S-E or S-$E_1$ wherein S, E and $E_1$ are as already defined; (h) subsequent to hydrogenation about 0-10% of the styrene double bonds have been hydrogenated and at least 80% of the conjugated diene double bonds have been hydrogenated; and (i) the molecular weight of each of the S blocks is from 4,000 to 12,000 daltons.

DETAILED DESCRIPTION OF THE PREFERRED EMBODIMENTS

In one embodiment, the present invention comprises an adhesive including a selectively hydrogenated block copolymer having an S block and an E or $E_1$ block and having the general formula:

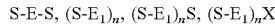

or mixtures thereof, wherein: (a) prior to hydrogenation, the S block is a polystyrene block; (b) prior to hydrogenation, the E block or $E_1$ block is a polydiene block, selected from the group consisting of polybutadiene, polyisoprene and mixtures thereof. The block copolymer can be linear or radial having three or four arms. General formulae for the linear configurations include:

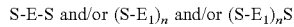

wherein the E block is a polydiene block, selected from the group consisting of polybutadiene, polyisoprene and mixtures thereof, having a molecular weight of from 40,000 to 120,000 daltons; the $E_1$ block is a polydiene block, selected from the group consisting of polybutadiene, polyisoprene and mixtures thereof, having a molecular weight of from 20,000 to 60,000 daltons; and n is 2. General formula for the radial configurations include:

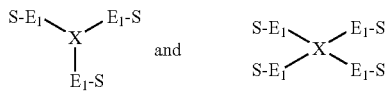

wherein the $E_1$ block is a polydiene block, selected from the group consisting of polybutadiene, polyisoprene and mixtures thereof, having a molecular weight of from 20,000 to 60,000 daltons; and X is a coupling agent residue.

The block copolymers useful with the present invention are prepared by anionic polymerization of styrene and a diene selected from the group consisting of butadiene, isoprene and mixtures thereof. The polymerization is accomplished by contacting the styrene and diene monomers with an organoalkali metal compound in a suitable solvent at a temperature within the range from about −150° C. to about 300° C., preferably at a temperature within the range from about 0° C. to about 100° C. Particularly effective anionic polymerization initiators are organolithium compounds having the general formula $RLi_n$ where R is an aliphatic, cycloaliphatic, aromatic, or alkyl-substituted aromatic hydrocarbon radical having from 1 to 20 carbon atoms; and n is an integer of 1 to 4. Preferred initiators include n-butyl lithium and sec-butyl lithium. Methods for anionic polymerization are well known and can be found in such references as U.S. Pat. Nos. 4,039,593 and U.S. Reissue Pat. No. Re 27,145.

The block copolymers useful with the method of the present invention can be linear sequential, linear coupled, or a radial block copolymer having a mixture of 2 to 6 "arms". Linear sequential block copolymers can be made by polymerizing styrene to form a first S block, adding butadiene to form an E block, and then adding additional styrene to form a second S block. A linear coupled block copolymer is made by forming the first S block and E block and then contacting the diblock with a difunctional coupling agent. A radial block copolymer is prepared by using a coupling agent that is at least trifunctional.

Difunctional coupling agents useful for preparing the linear block copolymers of the method of the present invention include, for example, methyl benzoate as disclosed in U.S. Pat. No.3,766,301. Other coupling agents having two, three or four functional groups useful for forming radial block copolymers include, for example, silicon tetrachloride and alkoxy silanes as disclosed in U.S. Pat. Nos. 3,244,664, 3,692,874, 4,076,915, 5,075,377, 5,272,214 and 5,681,895; polyepoxides, polyisocyanates, polyimines, polyaldehydes, polyketones, polyanhydrides, polyesters, polyhalides as disclosed in U.S. Pat. No. 3,281,383; diesters as disclosed in U.S. Pat. No. 3,594,452; methoxy silanes as disclosed in U.S. Pat. No. 3,880,954; divinyl benzene as disclosed in U.S. Pat. No. 3,985,830; 1,3,5-benzenetricarboxylic acid trichloride as disclosed in U.S. Pat. No. 4,104,332; glycidoxytrimethoxy silanes as disclosed in U.S. Pat. No. 4,185, 042; and oxydipropylbis(trimethoxy silane) as disclosed in U.S. Pat. No. 4,379,891.

In one embodiment of the present invention, the coupling agent used to prepare the block copolymer useful in the adhesives of the present invention is an alkoxy silane of the general formula $R_x$—Si—$(OR')_y$, where x is 0 or 1, x+y=3 or 4, R and R' are the same or different, R is selected from aryl, linear alkyl and branched alkyl hydrocarbon radicals, and R' is selected from linear and branched alkyl hydrocarbon radicals. The aryl radicals preferably have from 6 to 12 carbon atoms. The alkyl radicals preferably have 1 to 12 carbon atoms, more preferably from 1 to 4 carbon atoms. Under melt conditions these alkoxy silane coupling agents can couple further to yield functionalities greater than 4. Preferred tetra alkoxy silanes are tetramethoxy silane ("TMSi"), tetraethoxy silane ("TESi"), tetrabutoxy silane ("TBSi"), and tetrakis(2-ethylhexyloxy)silane ("TEHSi"). Preferred trialkoxy silanes are methyl trimethoxy silane ("MTMS"), methyl triethoxy silane ("MTES"), isobutyl trimethoxy silane ("IBTMO") and phenyl trimethoxy silane ("PhTMO"). Of these the more preferred are tetraethoxy silane and methyl trimethoxy silane.

One important aspect of the block copolymers useful with the present invention is the microstructure of the polymer. The microstructure relevant to the present invention is a high amount of 1,2 configuration, hereinafter referred to as vinyl content, in the E and/or $E_1$ blocks. This configuration can be achieved by the use of a control agent during polymerization of the diene. A typical agent is diethyl ether. See U.S. Pat. No. Re 27,145 and U.S. Pat. No. 5,777,031, the disclosure of which is hereby incorporated by reference. Any microstructure control agent known to those of ordinary skill in the art of preparing block copolymers to be useful can be used to prepare the block copolymers useful with the present invention.

In the practice of the present invention, the block copolymers used to prepare adhesives have from about 72 to about 90 mol percent vinyl in the E and/or $E_1$ blocks prior to hydrogenation. In another embodiment, the block copolymers have from about 73 to about 85 mol percent vinyl content. In still another embodiment, the block copolymers have from about 76 to about 78 mol percent vinyl content.

In one embodiment, the present invention is an adhesive prepared using a hydrogenated block copolymer. The hydrogenated block copolymers useful with the present invention are selectively hydrogenated using any of the several hydrogenation processes know in the art. For example, the hydrogenation may be accomplished using methods such as those taught, for example, in U.S. Pat. Nos. 3,494,942; 3,634,594; 3,670,054; 3,700,633; and Re. 27,145, the disclosures of which are hereby incorporated by reference. Any hydrogenation method that is selective for the double bonds in the conjugated polydiene blocks, leaving the aromatic unsaturation in the polystyrene blocks substantially intact, can be used to prepare the hydrogenated block copolymers useful with the present invention.

The methods known in the prior art and useful for preparing the hydrogenated block copolymers useful with the present invention involve the use of a suitable catalyst, particularly a catalyst or catalyst precursor comprising an iron group metal atom, particularly nickel or cobalt, and a suitable reducing agent such as an aluminum alkyl. Also useful are titanium based catalyst systems. In general, the hydrogenation can be accomplished in a suitable solvent at a temperature within the range from about 20° C. to about 100° C., and at a hydrogen partial pressure within the range from about 100 psig (689 kPa) to about 5,000 psig (34,473 kPa). Catalyst concentrations within the range from about 10 ppm to about 500 ppm by wt of iron group metal based on total solution are generally used and contacting at hydrogenation conditions is generally continued for a period of time with the range from about 60 to about 240 minutes. After the hydrogenation is completed, the hydrogenation catalyst and catalyst residue will, generally, be separated from the polymer.

In the practice of the present invention, an adhesive is prepared using hydrogenated block copolymers that have a hydrogenation degree greater than 80 percent. This means that more than from 80 percent of the conjugated diene double bonds in the E or $E_1$ block has been hydrogenated from an alkene to an alkane. In one embodiment, the E or $E_1$ block of the block copolymer has a hydrogenation degree greater than about 90 percent. In another embodiment, the E or $E_1$ block has a hydrogenation degree greater than about 95 percent.

In the practice of the present invention, the styrene content of the block copolymer used to prepare an adhesive is from about 10 percent to about 40 weight percent. In one embodiment, the styrene content of the block copolymer is from about 15 percent to about 24 percent. A block copolymer having any styrene content within these ranges can be used with the method of the present invention. Subsequent to hydrogenation, from 0 to 10 percent of the styrene double bonds in the S blocks have been hydrogenated in the practice of the present invention.

The molecular weight of each of the S blocks in the block copolymers useful for preparing the adhesives of the present invention is from about 4,000 to about 12,000 daltons. In one embodiment, the molecular weight of each of the S blocks is from about 5,800 to about 6,600 daltons. The S blocks of the block copolymers useful with the present invention can be a polystyrene block having any molecular weight within these ranges.

In the practice of the present invention, the E blocks of the block copolymers are a single polydiene block. These polydiene blocks can have molecular weights that range from about 40,000 daltons to about 120,000 daltons. The $E_1$ block is a polydiene block having a molecular weight range of from about 20,000 daltons to about 60,000 daltons. In one embodiment, the molecular weight range of the E block is from about 45,000 daltons to about 60,000 daltons, and the molecular weight range for each $E_1$ block of a coupled block copolymer, prior to being coupled, is from about 22,500 to about 30,000 daltons.

For the purposes of the present invention, the term "melt index" is a measure of the melt flow of the polymer according ASTM D1238 at 230° C. and 2.16 kg weight. It is expressed in units of grams of polymer passing through a melt rheometer orifice in 10 minutes. The hydrogenated block copolymers useful for preparing the adhesives of the present invention have a desirable high melt index allowing for easier processing than similar hydrogenated block copolymers that have higher melt indexes. In one embodiment, the hydrogenated block copolymers have a melt index of from 10 to 100. In another embodiment, the hydrogenated block copolymers have a melt index of from 20 to 90. In still another embodiment, the hydrogenated block copolymers have a melt index of from 40 to 60.

In the practice of the process of the present invention, a process for preparing an amorphous polyolefin and a selectively hydrogenated block copolymer are admixed. The amorphous polyolefin can be selected from the group consisting of homopolymers, copolymers, and terpolymers of $C_2$-$C_8$ alpha-olefins, and mixtures thereof. In one embodiment, the amorphous polyolefin is a copolymer of propylene and 1-butene or a terpolymer also having ethylene, and having a viscosity of from about 400 cps to about 8500 cps at 190° C. and a softening point of from about 95° C. to about 125° C. For the purposes of the present invention, the softening point is as determined using ASTM D36-95. In another embodiment, the amorphous polyolefin is a propylene/ethylene copolymer having a viscosity of from about 400 cps to about 8500 cps at 190° C. and a softening point of from about 125° C. to about 165° C. In still another embodiment, the amorphous polyolefin is a blend of homopolypropylene and propylene/ethylene copolymer having a viscosity of from about 400 cps to about 8500 cps at 190° C. and a softening point of from about 125° C. to about 165° C.

While any amorphous polyolefin compatible with block copolymer can be used, those polymerized in a process employing a catalyst selected from the group consisting of Ziegler-Natta catalysts, metallocene catalysts, vanadium catalysts, and mixtures thereof are particularly useful in the present application. Such polymers will have a density of from 0.85 to about 0.90 g/cc at 25° C. Preferably, the amorphous polyolefin useful in the process of the present invention has a molecular weight distribution (Mw/Mn) of from about 2 to about 5.

Of the two primary components used to prepare the adhesives of the present invention, a block copolymer and a polyolefin, the polyolefin is most often the less expensive and therefore used in as high of a concentration as possible in comparison to the block copolymer. For example, in the practice of the present invention, the amorphous polyolefin can be present in a weight percent of from about 99 percent to about 45 percent and the selectively hydrogenated block copolymer can be present in a weight percent of from about 1 percent to about 55 percent. In another embodiment, the amorphous polyolefin is present in a weight percent of from about 95 percent to about 50 percent and the selectively hydrogenated block copolymer is present in a weight percent of from about 5 percent to about 50 percent.

It is sometimes desirable to use additives in adhesives. Exemplary of such additives are members selected from the group consisting of other block copolymers, tackifying resins, end block resins, polymer extending oils, waxes, fillers, reinforcements, lubricants, stabilizers, and mixtures thereof.

When the additives used with the adhesives of the present invention are tackifying resins, exemplary resins include polystyrene block compatible resins and midblock compatible resins. The polystyrene block compatible resin may be selected from the group of coumarone-indene resin, polyindene resin, poly(methyl indene) resin, polystyrene resin, vinyltoluene-alphamethylstyrene resin, alphamethylstyrene resin and polyphenylene ether, in particular poly(2,6-dimethyl-1,4-phenylene ether). Such resins are e.g. sold under the trademarks "HERCURES", "ENDEX", "KRISTALEX", "NEVCHEM" and "PICCOTEX". Resins compatible with the hydrogenated (mid) block may be selected from the group consisting of compatible C5 hydrocarbon resins, hydrogenated C5 hydrocarbon resins, styrenated C5 resins, C5/C9 resins, styrenated terpene resins, fully hydrogenated or partially hydrogenated C9 hydrocarbon resins, rosins esters, rosins derivatives and mixtures thereof. These resins are e.g. sold under the trademarks "REGALITE", "REGALREZ", "ESCOREZ" and "ARKON". Also, one may use both a polystyrene block compatible resin and a midblock compatible resin.

In one embodiment of the present invention, a tackifying resin is used and it is selected from the group consisting of aliphatic petroleum resins and the hydrogenated derivatives thereof, aromatic petroleum resins and the hydrogenated derivatives thereof, aliphatic/aromatic petroleum resins and the hydrogenated derivatives thereof, hydrocarbon resins, styrene resins, alpha-methyl styrene resins, polyterpene resins, copolymers and terpolymers of natural terpene resins, pentaerythritol esters of wood, gum, and tall-oil rosins, glycerol esters of wood, gum, and tall-oil rosins, mixed esters of rosins and mixtures thereof. In embodiments including a tackifying resin, it can be present in a weight percent of from 10 to 80 weight percent. For example in one embodiment, the tackifying resin is present in a weight percent of from 30 to 55 weight percent.

Another embodiment of the present invention is an adhesive including a tackifying resin, an oil, or both. When an oil is used, it can be any oil that is compatible with the rest of the components. For example, the oil can be selected from the group consisting of mineral oils, naphthenic oils, paraffinic oils, and low molecular weight liquid polyolefin polymers. Any oil known to be useful in preparing adhesives to those of ordinary skill in the art can be used with the process of the present invention.

While the above referenced additives can be used, it is often desirable to limit their use. In one embodiment, the total concentration of additives present in an adhesive of the present invention is from about 0.001 percent to about 80 percent by weight. In another embodiment the total concentration of additives present is from about 0.001 percent to about 50 percent by weight. In still another embodiment the total concentration of additives present is from about 0.001 percent to about 25 percent by weight. Another embodiment of the present invention includes one where the total concentration of additives present is from about 0.001 percent to about 10 percent by weight. When the additive is a tackifying resin, it can be used in an amount of from about 10 to about 80 percent or about 30 to about 55 percent by weight. When the additive is an oil, it can be used at of from about 1 to about 30 weight percent.

The adhesives of the present invention may be used in a large number of applications, either as a neat polymer or in a compound. For example, the adhesive can be used in a laminate. In this application, an article of manufacture comprising a substrate and adherent thereto an adhesive is prepared. Exemplary of such materials is a book or magazine binding. The present invention can be used in many other end uses. For example, the adhesives of the present invention can be an article of manufacture selected from the group consisting of: disposable diapers; sanitary napkins; tampons; pant liners; adult incontinence pads; coverstock for feminine hygiene products; surgical and dental sponges; bandages; patient underpads; wipes; domestic wipes; industrial wipes; packaging; medical tray pads; fenestration drapes; filters; spill control materials; waste management materials; protective articles; operating gowns; mortuary pads; cable wrap; food tray pads; food preservation articles; seed germination pads; household pet litter; roofing materials; automotive trim; furniture; bedding; clothing; tapes; labels; and soil modifiers. The adhesives of the present invention can be used to prepare cases, cartons, and trays.

The adhesive can be used in several forms as well. For example the adhesives of the present invention can be a hot melt adhesive. In another embodiment, the adhesive can be a tacky, or pressure sensitive adhesive. The adhesives of the present invention can be employed in any form known to be useful to those of ordinary skill in the art of employing adhesives.

The adhesives of the present invention are prepared using a selectively hydrogenated block copolymer and an amorphous polyolefin. These components in conventional adhesives are generally not compatible and require special treatment in preparing an adhesive or else the use of a compatibilizer. The increased compatibility of the block copolymer and the polyolefin can result in adhesives having better physical properties and high temperature performance while being easier to process than similar conventional adhesives. Another benefit of the present invention is the ability to formulate an adhesive for use in applications that are sensitive to the use of compatibilizing additives.

The adhesives of the present invention can be prepared using any process known to be useful to those of ordinary skill in the art of preparing adhesives from formulations including block copolymers. For example, the adhesives of the present invention can be prepared using a process for preparing an adhesive comprising admixing an amorphous polyolefin and a selectively hydrogenated block copolymer having an S block and an E or $E_1$ block and having the general formula:

$$S\text{-}E\text{-}S, (S\text{-}E_1)_n, (S\text{-}E_1)_nS, (S\text{-}E_1)_nX$$

or mixtures thereof, wherein: (a) prior to hydrogenation the S block is a polystyrene block; (b) prior to hydrogenation the E block is a polydiene block, selected from the group consisting of polybutadiene, polyisoprene and mixtures thereof, having a molecular weight of from 40,000 to 120,000 daltons; (c) prior to hydrogenation the $E_1$ block is a polydiene block, selected from the group consisting of polybutadiene, polyisoprene and mixtures thereof, having a molecular weight of from 20,000 to 60,000 daltons; (d) n is an integer having a value of 2 to 6 and X is a coupling agent residue; (e) the styrene content of the block copolymer is from 10 percent to 40 weight percent; (f) the vinyl content of the polydiene block prior to hydrogenation is from 72 to 90 mole percent; (g) the block copolymer includes less than 25 weight percent lower molecular weight units having the general formula:

$$S\text{-}E \text{ or } S\text{-}E_1$$

wherein S, E and $E_1$ are as already defined; (h) subsequent to hydrogenation about 0-10% of the styrene double bonds have been hydrogenated and at least 80% of the conjugated diene double bonds have been hydrogenated; and (i) the molecular weight of each of the S blocks is from 4,000 to 12,000 daltons. The adhesives can be admixed and formed using any functional method.

An adhesive can also be prepared without using an amorphous polyolefin. For example, a low viscosity pressure sensitive adhesive (PSA) is prepared using a block copolymer prepared by anionic polymerization of styrene and then butadiene in the presence of a microstructure control agent followed by coupling and then hydrogenation. The block copolymer has a vinyl content of 76% determined using $^1$H NMR, a polystyrene equivalent GPC Mn molecular weight of 85,000 determined using a refractive index detector, and a 22% polystyrene content determined using $^1$H NMR. The styrene blocks have a molecular weight by GPC of about 6,000. This block copolymer is admixed with an oil; an antioxidant; and a tackifying resin described as a hydrogenated hydrocarbon resin, sold under the trade designation REGALITE R-91. The oil is a paraffinic oil, sold under the trade designation DRAKEOL 34. The antioxidant is IRGANOX 1010. The adhesive components are combined as solid components and mixed using a sigma blade mixer. The viscosity of the hot-melt adhesive is measure at 177° C. using a Brookfield viscometer. The formulated solid adhesive is then dissolved in toluene to achieve a 40% by weight solution. Adhesive test pieces are prepared by casting the formulation on MYLAR films and drying at room temperature for 1 hour and then in vacuum at 40° C. for 4 hours. The formulation composition and resulting adhesive properties are listed in Table I.

This shows that the high vinyl block copolymer comprising this adhesive formulation yields a tacky pressure sensitive adhesive having a relatively low viscosity. In contrast, for example, a conventional tacky adhesive can be prepared using a similar block copolymer, but one having lower vinyl content, such as a block copolymer having a vinyl content of 40 percent, a number average molecular weight of 50,000 and a styrene content of 30 weight percent. The formulation composition and resulting adhesive properties for this high visocisty adhesive are also listed in Table I.

TABLE I

| Composition, wt % | Low Viscosity PSA | High Viscosity PSA |
| --- | --- | --- |
| Block Copolymer | 30.0 | 30.0 |
| REGALITE R-91 | 44.2 | 50.0 |
| DRAKEOL 34 | 25.8 | 20.0 |
| IRGANOX 1010 | 0.1 | 0.1 |
| Rolling Ball Tack, cm | 5 | 4 |
| Polyken Probe Tack, kg | 0.30 | 0.38 |
| Loop Tack, oz/in | 58 | 85 |
| 180° Peel, pli | 1.8 | 2.2 |
| SAFT* to Mylar, ° C. | 70 | 86 |
| Viscosity, Pa · s | 1000 | 5950 |

*The SAFT measurements were made using a 1 inch by 1 inch overlap of adhesive test strip on stainless steel. A 500 g weight was suspended from the adhesive test strip and the temperature at which the test strip detached from the stainless steel substrate was measured.

EXAMPLES

The following examples are provided to illustrate the present invention. The examples are not intended to limit the scope of the present invention and they should not be so interpreted. Amounts are in weight parts or weight percentages unless otherwise indicated.

Example 1

A two component adhesive is prepared. The first component is a hydrogenated block copolymer prepared by anionic polymerization of styrene and then butadiene in the presence of a microstructure control agent followed by coupling and then hydrogenation. The block copolymer has a vinyl content of 76% determined using $^1$H NMR, a polystyrene equivalent GPC Mn molecular weight of 85,000 determined using a refractive index detector, and a 22% polystyrene content determined using $^1$H NMR. The styrene blocks have a molecular weight by GPC of about 6,000. The second component is a polyolefin sold under the trade designation REXTAC 2730 by HUNTSMAN POLYMERS and is described as a Butene-1/propylene copolymer with a softening point of 107° C., and viscosity at 190° C. of 3000 cps (3.0 pascal seconds). The molecular weight by GPC using toluene as a solvent and a polystyrene standard is Mw 51500 and Mn 15,550 which gives a polydispersity (Mw/Mn) of 3.3.

50 parts by weight of each component and 0.5 parts of an antioxidant, sold under the trade designation IRGANOX 1010 are admixed as a melt mix in a sigma mixer under a $N_2$ pad at 350-400° F. (177-204° C.). The resulting admixture is examined. It has a smooth appearance.

Comparative Example A

An adhesive is prepared and tested substantially identically to Example 1 except that the block copolymer has a vinyl content of 40 percent, a number average molecular weight of 50,000 and a styrene content of 30 weight percent. The resulting admixture is grainy in appearance.

Comments Regarding Example 1 and Comparative Example A

This example and comparative example demonstrate that block copolymers having a high vinyl content in the midblock are more compatible with polyolefins than those that have less vinyl content.

Example 2

A three component adhesive is prepared. The first component is the hydrogenated block copolymer used in Example 1. The second component is the polyolefin used in Example 1. The third component is sold under the trade designation EASTOTAC H-100W by Eastman and is described as a hydrogenated $C_5$ aliphatic tackifying resin having a 100° C. softening point.

16.5 parts by weight of the block copolymer, 50 parts of the REXTAC 2730, 33.5 parts of the EASTOTAC H-100W and 0.5 parts of IRGANOX 1010 are admixed as a melt mix in a sigma mixer under a $N_2$ pad at 350-400° F. (177-204° C.). The resulting admixture is examined. It has a smooth appearance. The RING AND BALL softening point is 212° F. (100° C.) as determined using ASTM D3695. The Brookfield viscosity at 350° F. (177° C.) is 4792 cps (4.79 pascal seconds).

The adhesive is formed into a tensile specimen by weighing a known weight of adhesive into in a release paper "boat" with known area and then heating the adhesive to 350° F. (177° C.) for about 1 hour during which time the adhesive flows to form a film of pre-defined thickness. The resulting film is tested according to ASTM D412. The results are displayed below in Table II.

Comparative Example B

An adhesive is prepared and tested substantially identically to Example 2 except that the block copolymer is the block copolymer used in Comparative Example A. The resulting admixture is grainy in appearance. The RING AND BALL softening point is 211° F. (99° C.). The Brookfield viscosity at 350° F. (177° C.) is 6667 cps (6.67 pascal seconds).

The adhesive is not formed into a tensile specimen because the adhesive admixture phase separates and forms two layers when an attempt is made to form the tensile specimen.

Example 3

An adhesive is prepared substantially identically to Example 2 except that 20 parts by weight of the block copolymer, 30 parts of the REXTAC 2730, 50 parts of the EASTOTAC H-100W and 0.5 parts of IRGANOX 1010 are admixed. The resulting admixture is examined. It has a smooth appearance. The RING AND BALL softening point is 223° F. (106° C.). The Brookfield viscosity at 350° F. (177° C.) is 3665 cps (3.66 pascal seconds).

The adhesive is formed into a tensile specimen and tested according to ASTM D412. The results are displayed below in Table II.

TABLE II

|  | Example 2 | Comparative Example B | Example 3 |
|---|---|---|---|
| Appearance | 1 Layer | 2 Layers | 1 layer |
| Thickness, inch (cm) | 0.069 (0.175) | Not Tested | 0.054 (0/137) |
| 50% Modulus psi (kPa) | 26 (179) | Not Tested | 44 (203) |
| 100% Modulus psi (kPa) | 30 (207) | Not Tested | 43 (296) |
| 300% Modulus psi (kPa) | 35 (241) | Not Tested | 60 (414) |
| 500% Modulus psi (kPa) | 26 (179) | Not Tested | 105 (724) |
| Max stress psi (kPa) | 40 (276) | Not Tested | 310 (2140) |
| Stress at break psi (kPa) | 11 (76) | Not Tested | 311 (2140) |
| Elongation at break, % | 742 | Not Tested | 945 |

Comments Regarding Example 2 and Comparative Example B

This example and comparative example also show that the block copolymer having a higher vinyl content is more compatible with the polyolefin.

Example 4

An adhesive is prepared substantially identically to Example 1 except that 16.5 parts by weight of the block copolymer of claim 1, 50 parts of EASTOFLEX M1030S which is described by the supplier as an ethylene/propylene copolymer with a softening point of 150° C. and viscosity at 190 deg C. of 3000 cps, 33.5 parts of the EASTOTAC H-100W and 0.5 parts of IRGANOX 1010 are admixed. The resulting admixture is examined. It has a smooth appearance. The RING AND BALL softening point is >260° F. (>127° C.). The Brookfield viscosity at 350° F. (177° C.) is 5275 cps (5.28 pascal seconds).

Example 5

An adhesive is prepared substantially identically to Example 1 except that 20 parts by weight of the block copolymer of claim 1, 60 parts of EASTOTAC H-100W, 5 parts of REXTAC 2730, 15 parts of DRAKEOL 34 which is described by the supplier, PENRECO, as a white mineral oil with a 40° C. 75 centistokes (45 cm²/min) viscosity, and 0.5 parts of IRGANOX 1010 are admixed. The resulting admixture is examined. It has a smooth appearance. The RING AND BALL softening point is 178° F. (81° C.). The Brookfield viscosity at 350° F. (177° C.) is 638 cps (0.64 pascal seconds).

Example 6

An adhesive is prepared substantially identically to Example 1 except that 12.5 parts by weight of the block copolymer of claim 1, 60 parts of EASTOTAC H-100W, 12.5 parts of REXTAC 2730, 15 parts of DRAKEOL 34, and 0.5 parts of IRGANOX 1010 are admixed. The resulting admixture is examined. It has a smooth appearance. The RING AND BALL softening point is 169° F. (76° C.). The Brookfield viscosity at 350° F. (177° C.) is 468 cps (0.47 pascal seconds).

Comments Regarding Examples 4, 5, and 6

Example 4 is an example of an adhesive including an ethylene/propylene copolymer. Examples 5 and 6 are examples of adhesives of the present invention including an oil.

What is claimed is:

1. An adhesive comprising an amorphous polyolefin and a selectively hydrogenated block copolymer having an S block and an E or $E_1$ block and having the general formula:

$$S\text{-}E\text{-}S, (S\text{-}E_1)_n, (S\text{-}E_1)_nS, (S\text{-}E_1)_nX$$

or mixtures thereof, wherein:
(a) prior to hydrogenation the S block is a polystyrene block;
(b) prior to hydrogenation the E block is a polydiene block, selected from the group consisting of polybutadiene and mixtures of polybutadiene and polyisoprene, having a molecular weight of from 40,000 to 120,000 daltons;
(c) prior to hydrogenation the $E_1$ block is a polydiene block, selected from the group consisting of polybutadiene and mixtures of polybutadiene and polyisoprene, having a molecular weight of from 20,000 to 60,000 daltons;
(d) n is an integer having a value of 2 to 6 and X is a coupling agent residue;
(e) the styrene content of the block copolymer is from 10 percent to 40 weight percent;
(f) the vinyl content of the polydiene block prior to hydrogenation is from 72 to 90 mole percent;
(g) the block copolymer includes less than 25 weight percent lower molecular weight units having the general formula:

$$S\text{-}E \text{ or } S\text{-}E_1$$

wherein S, E and $E_1$ are as already defined;
(h) subsequent to hydrogenation about 0-10% of the styrene double bonds have been hydrogenated and at least 80% of the conjugated diene double bonds have been hydrogenated; and (i) the molecular weight of each of the S blocks is from 4,000 to 12,000 daltons;

(j) the amorphous polyolefin is selected from the group consisting of a copolymer of propylene and 1-butene or a terpolymer also having ethylene, and having a viscosity of from about 400 cps to about 8500 cps at 190° C. and a softening point of from about 95° C. to about 125° C., a propylene/ethylene copolymer having a viscosity of from about 400 cps to about 8500 cps at 190° C. and a softening point of from about 125° C. to about 165° C., and a blend of homopolypropylene and propylene/ethylene copolymer having a viscosity of from about 400 cps to about 8500 cps at 190° C. and a softening point of from about 125° C. to about 165° C.

2. The adhesive of claim 1 wherein the styrene content of the block copolymer is about 20 weight percent.

3. The adhesive of claim 1 wherein the vinyl content of the polydiene block prior to hydrogenation is from 73 to 85 mole percent.

4. The adhesive of claim 3 wherein the vinyl content of the polydiene block prior to hydrogenation is from 76 to 78 mole percent.

5. The adhesive of claim 1 wherein the E block is a polybutadiene having a molecular weight of from 45,000 to 60,000 daltons, or the $E_1$ block is two or more coupled polybutadiene blocks, each of the polybutadiene blocks, prior to being coupled, having a molecular weight of from 22,500 to 30,000 daltons.

6. The adhesive of claim 1 wherein the E or $E_1$ block has a degree of hydrogenation greater than 90%.

7. The adhesive of claim 1 wherein the block copolymer has a melt index at 230° C. and a 2.16 kg weight of from about 10 to about 100 grams/10 minutes determined according to ASTM 1238D.

8. The adhesive of claim 1 wherein the amorphous polyolefin is a copolymer of propylene and 1-butene or a terpolymer also having ethylene, and having a viscosity of from about 400 cps to about 8500 cps at 190° C. and a softening point of from about 95° C. to about 125° C.

9. The adhesive of claim 1 wherein the amorphous polyolefin is a propylene/ethylene copolymer having a viscosity of from about 400 cps to about 8500 cps at 190° C. and a softening point of from about 125° C. to about 165° C.

10. The adhesive of claim 1 wherein the amorphous polyolefin is a blend of homopolypropylene and propylene/ethylene copolymer having a viscosity of from about 400 cps to about 8500 cps at 190° C. and a softening point of from about 125° C. to about 165° C.

11. The adhesive of claim 1 wherein the amorphous polyolefin is polymerized in a process employing a catalyst selected from the group consisting of Ziegler-Natta catalysts, metallocene catalysts, vanadium catalysts, and mixtures thereof.

12. The adhesive of claim 1 wherein the amorphous polyolefin has a density of from 0.85 to about 0.90 g/cc at 25° C.

13. The adhesive of claim 1 wherein the amorphous polyolefin has a molecular weight distribution (Mw/Mn) of from about 2 to about 5.

14. The adhesive of claim 1 wherein the amorphous polyolefin is present in a weight percent of from about 99 percent to about 45 percent and the selectively hydrogenated block copolymer is present in a weight percent of from about 1 percent to about 55 percent.

15. The adhesive of claim 14 wherein the amorphous polyolefin is present in a weight percent of from about 95 percent to about 50 percent and the selectively hydrogenated block copolymer is present in a weight percent of from about 5 percent to about 50 percent.

16. The adhesive of claim 1 additionally comprising a tackifying resin.

17. The adhesive of claim 16 wherein the tackifying resin is selected from the group consisting of aliphatic petroleum resins and the hydrogenated derivatives thereof, aromatic petroleum resins and the hydrogenated derivatives thereof, aliphatic/aromatic petroleum resins and the hydrogenated derivatives thereof, hydrocarbon resins, styrene resins, alpha-methyl styrene resins, polyterpene resins, copolymers and terpolymers of natural terpene resins, pentaerythritol esters of wood, gum, and tall-oil rosins, glycerol esters of wood, gum, and tall-oil rosins, mixed esters of rosins and mixtures thereof.

18. The adhesive of claim 16 wherein the tackifying resin is present in a weight percent of from 10 to 80 weight percent.

19. The adhesive of claim 18 wherein the tackifying resin is present in a weight percent of from 30 to 55 weight percent.

20. The adhesive of claim 1 additionally comprising an oil.

21. The adhesive of claim 20 wherein the oil is selected from the group consisting of mineral oils, naphthenic oils, paraffinic oils, and low molecular weight liquid polyolefin polymers.

22. The adhesive of claim 20 wherein the oil is present at a weight percent of from about 1 to about 30 weight percent.

23. The adhesive of claim 16 additionally comprising an oil.

24. The adhesive of claim 23 wherein the oil is selected from the group consisting of mineral oils, naplithenic oils, paraffinic oils, and low molecular weight liquid polyolefin polymers.

25. The adhesive of claim 24 wherein the oil is present at a weight percent of from about 1 to about 30 weight percent.

26. An article of manufacture comprising a substrate and adherent thereto an adhesive of claim 1.

27. The article of manufacture of claim 26 wherein the article of manufacture is selected from the group consisting of: disposable diapers; sanitary napkins; tampons; pant liners; adult incontinence pads; coverstock for feminine hygiene products; surgical and dental sponges; bandages; patient underpads; wipes; domestic wipes; industrial wipes; packaging; medical tray pads; fenestration drapes; filters; spill control materials; waste management materials; protective articles; operating gowns; mortuary pads; cable wrap; food tray pads; food preservation articles; seed germination pads; household pet litter; roofing materials; automotive trim; furniture; bedding; clothing; and soil modifiers.

28. The article of manufacture of claim 26 wherein the article of manufacture is a magazine or book binding.

29. The article of manufacture of claim 26 wherein the adhesive is a hot-melt adhesive, tacky adhesive or a pressure sensitive adhesive.

30. The adhesive of claim 1 wherein the E block is a polybutadiene or the $E_1$ block is two or more coupled polybutadiene blocks.

* * * * *